(12) United States Patent
Courbriere et al.

(10) Patent No.: US 6,407,142 B1
(45) Date of Patent: Jun. 18, 2002

(54) USE OF STILBENE DERIVATIVES SUBSTITUTED IN POSITION 3 AS DEODORANT ACTIVE AGENTS IN COSMETIC COMPOSITIONS

(75) Inventors: Christophe Courbriere, Paris; Francis Pruche, Senlis; Sylvain Kravtchenko, Paris, all of (FR)

(73) Assignee: L'Oreal S.A., Paris (FR)

( * ) Notice: Subject to any disclaimer, the term of this patent is extended or adjusted under 35 U.S.C. 154(b) by 0 days.

(21) Appl. No.: 09/504,724

(22) Filed: Feb. 16, 2000

(30) Foreign Application Priority Data

Feb. 17, 1999 (FR) .......................................... 99 01931

(51) Int. Cl.⁷ .............................................. A61K 31/05
(52) U.S. Cl. ...................................................... 514/736
(58) Field of Search .......................................... 514/736

(56) References Cited

U.S. PATENT DOCUMENTS 2,776,986 A    1/1957    Sanderson

FOREIGN PATENT DOCUMENTS

FR          2 275 193         1/1976
WO         WO 00/21368        4/2000

OTHER PUBLICATIONS

Frykholm, Nature, vol. 155, , p. 454–455, Apr. 14, 1945.*
Chemical Abstracts, XP002122811, 1987 (RN 21956-56-9).
K.O. Frykholm, "Bacteriological Studies of Pinosylvine, its Monomethyl and Dimethyl Ethers, and Toxicologic Studies of Pinosylvine", Nature, vol. 155, Apr. 14, 1945, pp. 454–455.
Mitsuo Takahashi et al., "Constituents of the Plants of Coniferae and Allied Orders. XLIII. Distribution of Flavonoids and Stilbenoids of Coniferae Leaves", Journal of the Pharmaceutical Society of Japan, vol. 80, No. 10, Oct. 1960, pp. 1488–1492. (Abstract only).
Charles Fox, "An Introduction to Multiple Emulsions", Cosmetics and Toiletries, vol. 101, Nov. 1986, pp. 101–112.
English language Derwent Abstract of FR 2 275 193.

* cited by examiner

*Primary Examiner*—Barbara P. Badio
(74) *Attorney, Agent, or Firm*—Finnegan, Henderson, Farabow, Garrett & Dunner LLP

(57) ABSTRACT

The present invention relates to the use of 3,5-dihydroxystilbene or 3-hydroxystilbene and/or derivatives thereof as deodorant active agents in the preparation of cosmetic compositions, to the deodorant cosmetic compositions containing these compounds, to the use of the compositions for human topical application, and to novel stilbene derivatives substituted in position 3 and to the cosmetic compositions comprising them.

5 Claims, No Drawings

USE OF STILBENE DERIVATIVES SUBSTITUTED IN POSITION 3 AS DEODORANT ACTIVE AGENTS IN COSMETIC COMPOSITIONS

The present invention relates to the use of 3,5-dihydroxystilbene or 3-hydroxystilbene and/or derivatives thereof as deodorant active agents in the preparation of a cosmetic composition, to the deodorant cosmetic composition containing these compounds and to the use of the composition for human topical application. The invention also relates to a process for treating human underarm odors, which comprises applying an effective amount of the composition to the armpit area.

In the cosmetics field, it is a well-known practice to use, in topical application, deodorant products containing active substances of antiperspirant type or of bactericidal type to reduce or even eliminate underarm odors, which are generally unpleasant. Antiperspirants have the effect of limiting the flow of sweat. They generally consist of aluminium salts, which, on the one hand, are skin irritants and, on the other hand, reduce the flow of sweat by modifying the skin physiology, which is unsatisfactory. Bactericides inhibit the growth of the skin flora responsible for underarm odors. Among bactericidal products, the one most commonly used is Triclosan (2,4,4'-trichloro-2'-hydroxydiphenyl ether), which has the drawback of considerably modifying the ecology of the skin flora and of being inhibited by certain compounds such as, for example, nonionic surfactants, commonly used in the formulation of cosmetic compositions. Moreover, the insoluble nature of Triclosan in water does not allow it to be incorporated into essentially aqueous formulations.

With the aim of obtaining long-term efficacy, novel products are sought that exert a deodorant action, i.e., products capable of modifying, reducing and/or eliminating or preventing the development of body odor (this definition is given in the book "Cosmetic Science and Technology Series"—1988/Volume 7, chapter 10-IIIc, incorporated by reference herein). In addition, products are sought that do not have the drawbacks of the active substances used in the prior art. It is known that certain stilbene compounds, such as 4-hydroxystilbene and 3,5,4'-stilbene (or Resveratrol), make it possible to limit the development of sweat odor. However, the efficacy of these molecules is very markedly insufficient.

After considerable research conducted in this matter, the inventors have now discovered, surprisingly and unexpectedly, that the compounds of formula (I) defined below have the property of preventing the development of body odor, without the drawbacks of the active substances previously used in deodorant compositions, and with the advantage, for some of these compounds, of being water-soluble in proportions that are advantageous and sufficient to be easy to place in formulation, especially in water-based cosmetic compositions for human topical application. This discovery forms the basis of the present invention.

A first subject of the present invention is thus the use of compounds of formula (I) below as deodorant active agents in cosmetic compositions:

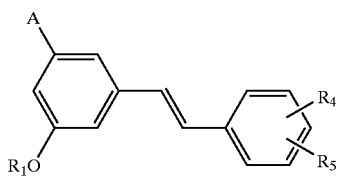

in which:
A denotes a hydrogen atom or a radical $OR_2$,
$R_1$ and $R_2$, which may be identical or different, denote a hydrogen atom; a $C_1-C_4$ alkyl radical; an acyl radical $R_3CO$ in which $R_3$ denotes a linear or branched, saturated or unsaturated, hydroxylated or non-hydroxylated, carboxylated or non-carboxylated $C_1-C_{30}$ hydrocarbon-based radical; a radical $PO(OX_1)(OX_2)$ or a radical $SO_2(OX_3)$ in which $X_1$, $X_2$ and $X_3$, which may be identical or different, denote a hydrogen atom or a monovalent alkali metal or $NH_4^+$ cation, in which $X_1$ and/or $X_2$ can also denote a divalent metal cation; a glycosyl radical; or a uronyl radical; and
$R_4$ and $R_5$, which are identical, denote a hydrogen atom or a hydroxyl radical.

A second subject of the invention is a deodorant cosmetic composition comprising at least one compound of formula (I) described above. Another subject of the invention is the use of the composition in or for the manufacture of deodorant cosmetic products intended for human topical application. Yet another subject of the invention is the use of at least one compound of formula (I) described above, as a selective inhibitor of certain bacterial species constituting the human skin flora, and, in particular, *Corynebacterium xerosis*. Still another subject of the invention is a process for treating human underarm odors, which comprises applying an effective amount of the composition to the armpit area.

A subject of the invention is also novel compounds of formula (I) as defined above, in which A denotes a hydrogen atom or a radical $OR_2$, $R_1$ and $R_2$, which may be identical or different, denote an acyl radical $R_3CO$ in which $R_3$ denotes a linear or branched, saturated or unsaturated, hydroxylated or non-hydroxylated, carboxylated or non-carboxylated $C_4-C_{30}$ hydrocarbon-based radical; a radical $PO(OX_1)(OX_2)$ or a radical $SO_2(OX_3)$ in which $X_1$, $X_2$ and $X_3$, which may be identical or different, denote a hydrogen atom or a monovalent alkali metal or $NH_4^+$ cation, in which $X_1$ and/or $X_2$ can also denote a divalent metal cation; or a uronyl radical, and $R_4$ and $R_5$, which are identical, denote a hydrogen atom or a hydroxy radical.

Another subject of the invention is a cosmetic composition comprising at least one compound of formula (I) defined above, in which A denotes a hydrogen atom or a radical $OR_2$, $R_1$ and $R_2$, which may be identical or different, denote an acyl radical $R_3CO$ in which $R_3$ denotes a linear or branched, saturated or unsaturated, hydroxylated or non-hydroxylated, carboxylated or non-carboxylated $C_1-C_{30}$ hydrocarbon-based radical; a radical $PO(OX_1)(OX_2)$ or a radical $SO_2(OX_3)$ in which $X_1$, $X_2$ and $X_3$, which may be identical or different, denote a hydrogen atom or a monovalent alkali metal or $NH_4^+$ cation, in which $X_1$ and/or $X_2$ can also denote a divalent metal cation; or a uronyl radical, and $R_4$ and $R_5$, which are identical, denote a hydrogen atom or a hydroxyl radical.

In formula (I) described above, the alkyl radicals can be linear or branched and, in particular, denote methyl, ethyl, propyl, isopropyl, n-propyl, butyl, n-butyl or tert-butyl radicals. Preferably, the alkyl radical denotes a methyl radical and the glycosyl radical denotes a saccharose or saccharide radical, such as arabinose, glucose, fructose or sucrose. More preferably, the glycosyl radical denotes a glucosyl radical; also preferably the uronyl radical denotes a mannuronyl or glucuronyl radical.

Among the compounds of formula (I) used according to the present invention, particular examples include 3,5-dihydroxystilbene (or Pinosylvine), its monomethyl and dimethyl ethers, 3,5,3',4'-tetrahydroxystilbene, and the corresponding mono- and diglycoside forms. Mention may also be made of 3-hydroxystilbene and its methyl ether.

In the present invention, the glucoside and glucuronide forms of these compounds of formula (I) are particularly advantageous since, on account of their water-solubility, they have the advantage of being easy to place in formulation in essentially an aqueous medium. In addition, they can release the active substance in situ under the action of glycosidases of bacterial origin, which are present under the armpits.

According to the invention, it is even more particularly preferred to use 3,5-dihydroxystilbene (or Pinosylvine), which, in comparison with Triclosan that is well known in the field under consideration, has the advantage of being more effective regarding deodorant activity, of being odorless at working concentrations, and of being more respectful to the skin's bacterial flora, since its bactericidal action is selective on *Corynebacterium xerosis*, the main strain producing perspiration odors.

The compounds of formula (I) according to the invention preferably represent 0.001 to 10% by weight approximately relative to the total weight of the deodorant cosmetic composition, more particularly, from 0.01 to 5%, and, even more particularly, from 0.1 to 5% by weight approximately relative to this weight.

The compounds of formula (I) described above, in which A denotes a hydrogen atom or a radical $OR_2$, and $R_1$ and $R_2$, which may be identical or different, denote a hydrogen atom; a $C_1$–$C_4$ alkyl radical or a glycosyl radical, are in natural form, especially in the plants of the genera:

Pinus, and, in particular, *Pinus montana mill., Pinus sylvestris L, Pinus contorta* var. *Latifolia S. Wats, Pinus ponderosa Dougl., Pinus Halpensis Mill.* from the Pinacea family;

Alnus, and, in particular, *Alnus sieboldiana* from the Betulacea family;

Polygonum, and, in particular, *Polygonum nodosum* from the Polygonacea family;

Dalbergia, and, in particular, *Dalbergia sissoo* from the Leguminosa family;

Scutellaria, and, in particular, *Scutellaria scandens* from the Lamiacea family;

Lindera, and, in particular, *Lindera reflexa* from the Lauracea family.

3,5-dihydroxystilbene and its monomethyl and dimethyl ethers can be extracted from the wood of plants of the genus Pinus; 3,5-dihydroxystilbene monoglucoside can be extracted from the roots of plants of the genus Scutellaria; 3,5-dihydroxystilbene diglucoside can be extracted from plants of the genus Lindera. 3,5,3',4'-Tetrahydroxystilbene (or Piceatannol or Astringenin) can be extracted from the wood of pine and spruce trees and from a leguminous plant (*Laburnum anagyroides*). 3,5-Dihydroxystilbene, 3-hydroxystilbene and 3,5,3',4'-tetrahydroxystilbene can be derived from plant extracts, as described above, and can be obtained by any extraction method known to those skilled in the art or can be obtained by synthesis according to methods that are generally well known in the literature. Particular examples include alcoholic extracts, especially ethanolic extracts, and aqueous-alcoholic extracts.

The deodorant cosmetic composition according to the invention can comprise, in addition to the compound(s) of formula (I) according to the invention, other deodorant or antiperspirant active agents conventionally used in this type of composition. For the purposes of the present invention, the expression "deodorant active agent" means any substance capable of reducing the flow of sweat and/or of masking, improving or reducing the unpleasant odor resulting from the decomposition of human sweat by bacteria. These deodorant active agents can be chosen, for example, from: water-soluble zinc salts such as, for example, zinc pyrrolidonecarboxylate (more particularly known as zinc pidolate), zinc sulphate, zinc chloride, zinc lactate, zinc gluconate and zinc phenolsulphonate; antiperspirant active agents, for instance aluminium salts such as, for example, aluminium chloride or aluminium hydroxyhalides, zirconium salts such as, for example, zirconium oxide salts or hydroxyzirconyl salts, metal complexes such as aluminium or zirconium with an amino acid such as, for example, glycine, as described in U.S. Pat. No. 3,792,068, incorporated herein by reference; bactericides such as 2,4,4'-trichloro-2'-hydroxydiphenyl ether (Triclosan) and 3,7,11-trimethyidodeca-2,5,10-trienol (Farnesol). These additional deodorant active agents can be present in the composition according to the invention in a proportion from about 0.001 to 20% by weight relative to the total composition, and, preferably, in a proportion from about 0.1 to 10% by weight.

The deodorant cosmetic composition according to the invention is conventionally formulated depending on the presentation form for which it is intended. It is preferably formulated in a cosmetically acceptable vehicle that may, in particular, be essentially aqueous, or may contain organic solvents and especially $C_1$–$C_4$ monoalcohols, preferably ethanol, to accelerate the evaporation of the product, or propylene glycol, dipropylene glycol or ethers thereof. The deodorant cosmetic composition according to the invention can also be formulated as a water-in-oil or oil-in-water emulsion or as a water-in-oil-in-water triple emulsion (such emulsions are known and described, for example, by C. Fox in "Cosmetics and Toiletries"—November 1986—Vol 101—pages 101–112, incorporated herein by reference).

The deodorant cosmetic composition of the invention can also comprise cosmetic adjuvants chosen from fatty substances, gelling agents, emollients, softeners, antioxidants, opacifiers, stabilizers, anti-foaming agents, moisturizers, vitamins, fragrances, preserving agents, surfactants, fillers, sequestering agents, polymers, propellants, acidifying or basifying agents, dyes, pigments, thickeners or any other ingredient usually used in cosmetics for this type of application. If surfactants are used, they are preferably chosen from anionic, amphoteric or nonionic surfactants. Needless to say, a person skilled in the art will take care to select this or these optionally additional compound(s) such that the advantageous properties intrinsically associated with the deodorant cosmetic composition according to the invention are not, or are not substantially, adversely affected by the addition(s) envisaged.

Fatty substances useful in the present invention can comprise an oil or a wax or a mixture thereof, petroleum jelly, paraffin, lanolin, hydrogenated lanolin or acetylated lanolin; they also comprise fatty acids, fatty alcohols such as lauryl alcohol, cetyl alcohol, myristyl alcohol, stearyl alcohol, palmityl alcohol, oleyl alcohol or 2-octyldodecanol, fatty acid esters such as glyceryl monostearate, polyethylene glycol monostearate, isopropyl myristate, isopropyl adipate, isopropyl palmitate, octyl palmitate, $C_{12}$–$C_{15}$ fatty alkyl benzoates (Finsolv TN from Finetex), myristyl alcohol polyoxypropylenated with 3 mol of propylene oxide (Witconol APM from Witco), $C_6$–$C_8$ fatty acid triglycerides such as caprylic/capric acid triglycerides.

When the fatty substances comprise or include oils, the oils are chosen from animal, plant, mineral and synthetic oils and, in particular, hydrogenated palm oil, hydrogenated castor oil, liquid petroleum jelly, liquid paraffin, purcellin oil (stearyl octanoate), silicone oils and isoparaffins. When the fatty substances comprise or include waxes, the waxes are chosen from animal, fossil, plant, mineral and synthetic waxes. Particular examples include beeswaxes, carnauba wax, candelilla wax, sugarcane wax, Japan wax, ozokerites, montan wax, microcrystalline waxes, paraffins and silicone waxes and resins.

Thickeners useful in the present invention, which are preferably nonionic, can be chosen from modified or unmodified guar gums and celluloses, such as hydroxypropyl guar gum, cetylhydroxyethylcellulose, silicas such as, for example, Bentone Gel MiO sold by the company NL Industries or Veegum Ultra sold by the company Polyplastic.

The deodorant cosmetic composition can comprise emollients, which contribute towards a soft, dry, non-sticky sensation when the composition is applied to the skin. These emollients can be chosen from products such as volatile silicones, non-volatile silicones and other non-volatile emollients.

The volatile silicones are defined, in a known manner, as compounds that are volatile at room temperature. Among these compounds, mention may be made of cyclic, linear volatile silicones of the dimethylsiloxane type whose chains comprise from 3 to 9 silicone residues. Cyclomethicone D4 or D5 is preferably chosen.

The non-volatile silicones are defined, in a known manner, as compounds with a low vapour pressure at room temperature. Among these compounds are included: polyalkylsiloxanes, in particular, linear polyalkylsiloxanes such as, for example, polydimethylsiloxanes, or linear dimethicones, sold by the company Dow Corning under the name "Dow Corning 200 Fluid"; polyalkylarylsiloxanes such as, for example, the polymethylphenylsiloxanes sold by the company Dow Corning under the name "Dow Corning 556 Fluid"; polyether and siloxane copolymers such as, for example, dimethicone copolyols.

Among the non-volatile emollients that can be used in the present invention, examples include: hydrocarbon-based derivatives, mineral oils, fatty alcohols, esters of $C_3$–$C_{18}$ alcohols with $C_3$–$C_{18}$ acids, esters of benzoic acid with $C_{12}$–$C_{18}$ alcohols and mixtures thereof, $C_2$–$C_6$ polyols preferably chosen from glycerol, propylene glycol and sorbitol, and polyalkylene glycol polymers.

The amounts of these various constituents that may be present in the deodorant cosmetic composition according to the invention are those which are conventionally used for the presentation forms under consideration.

The deodorant composition according to the invention can be in the form of a lotion, a cream or a fluid gel distributed as an aerosol spray, in a pump-dispenser bottle or as a roll-on, in the form of a thickened cream distributed in a tube and in the form of a stick or powder, and, in this respect, can contain the ingredients and propellants generally used in products of this type and which are well known to those skilled in the art.

The present invention is further illustrated by the following examples which are designed to teach those of ordinary skill in the art how to practice the invention. The following examples are merely illustrative of the invention and should not be construed as limiting the invention as claimed.

EXAMPLE 1

In vitro Test of Evaluation of Odors

This example compared the efficacy of Pinosylvine (invention) against that of deodorant active agents of the prior art (Triclosan, Resveratrol, 4-hydroxystilbene). A test of inhibition of the evolution of odors was carried out on natural sweat. This test is carried out by adding the deodorant agent to fresh sweat, and then in carrying out an olfactory evaluation by means of a jury of experts after incubation at 37° C. for 18 hours and 24 hours. Thus, underarm sweat was collected in a sauna from several human models and combined to form a sample of sweat. In order to obtain the characteristic nauseating odor of sweat, before introducing the active substance, this sample of sweat was incubated for 18 hours at a temperature of 37° C. 1 ml of the incubated sample of sweat was introduced into each flask of active substance to be tested as well as into a control flask (without active substance). The active substance was then introduced into each of the flasks to be tested.

1) After incubation for 18 hours, the odor of each flask was evaluated.

The odor was evaluated on the basis of 2 criteria:

(a)—overall intensity (grading from 0 to 4):

| 0 | 1 | 2 | 3 | 4 |
|---|---|---|---|---|
| zero | mild | moderate | strong | very strong |

(b)—the hedonistic assessment (grading from 0 to 6):

| 0 | 1 | 2 | 3 | 4 | 5 | 6 |
|---|---|---|---|---|---|---|
| very pleasant | pleasant | mildly pleasant | neutral | mildly unpleasant | unpleasant | very unpleasant |

2) The flasks were reincubated in an oven at 37° C. for 6 h, the total desired incubation time being 24 h. Evaluation of the odor of each flask was then repeated as before.

3) Results:

The results were given as percentages of variation (reduction) of the odor and of the hedonistic grade relative to the control sweat without deodorant agent:

| Deodorant agent | amount A.M. mg/ml of sweat | average % of reduction in the odor intensity (T18 h, T24 h) | average % of reduction in the unpleasantness of the odor (T18 h, T24 h) |
|---|---|---|---|
| Pinosylvine | 1 | −77 | −33 |
|  | 2 | −89 | −40 |
| Triclosan | 1 | −64 | −26 |
|  | 2 | −64 | −26 |
| Resveratrol | 1 | −21 | −14 |
|  | 2 | −25 | −12 |

-continued

| Deodorant agent | amount A.M. mg/ml of sweat | average % of reduction in the odor intensity (T18 h, T24 h) | average % of reduction in the unpleasantness of the odor (T18 h, T24 h) |
|---|---|---|---|
| 4-Hydroxy-stilbene | 1 | −18 | −3 |
|  | 2 | −21 | −10 |

The results demonstrate that Pinosylvine produces a very large reduction in the intensity and unpleasantness of the odor of natural sweat for at least 24 h; the deodorant efficacy (reduction in the intensity and unpleasantness of the odor) of Pinosylvine was greater than that of Triclosan, Resveratrol and 4-hydroxystilbene; it was also noted that these last two compounds had highly insufficient efficacy.

EXAMPLE 2

Determination of the Biocidal Activity

Determination of the microbiostatic activity of Pinosylvine was carried out comparatively with Triclosan and Resveratrol (deodorant active agents of the prior art), by the method of dilutions in agar medium. Each of the 3 compounds was presented in the form of an ethanolic solution. 100 µl of the ethanolic solution were added to 1.9 ml of agar culture heated beyond the melting point to 45° C. (medium chosen as a function of the nutrient requirements of the test strain). After stirring with a Vortex machine, successive dilutions, in geometrical progression by a factor of 2, of the solution obtained were carried out using agar culture medium heated beyond its melting point to 45° C. 1 ml of each dilution was introduced into the wells of a microplate (flask, 24 wells). Four µl of microbial suspension were placed at the surface of the agar medium. Two control wells were also prepared: 100 µl $H_2O$+1.9 ml of culture medium (growth control), 100 ml ethanol+1.9 ml of culture medium (control of non-toxicity of the ethanol diluted to 1/20).

After incubation under conditions (temperature, atmosphere and duration) dependent on the test strain, the minimum inhibitory concentration (MIC) was given by the lowest concentration of product which inhibited the microbial growth. The results, shown below, are expressed in µg/ml.

For the control cupules ($H_2O$ or ethanol), the observation of microbial growth made it possible to exclude the presence of a placebo effect.

|  | MIC µg/ml | | |
|---|---|---|---|
|  | Pinosylvine | Triclosan | Resveratrol |
| *Staphylococcus aureus* . . . | 200 | 0.1 | 72 |
| *Staphylococcus epidermis* . . . | 400 | 2.3 | 72 |
| *Corynebacterium xerosis* . . . | 6 | 2.3 | 14 |
| *Propionibacterium acnes* . . . | 200 | 2.3 | 29 |
| *Pityrosporum ovale* . . . | >400 | >144 | >115 |
| *Aspergillus niger* . . . | 400 | 18.1 | >115 |

The results demonstrate that:
(i) the biocidal activity of Pinosylvine was less than that of Resveratrol, on all the strains tested except for the *Corynebacterium xerosis* strain; the bactericidal activity of Pinosylvine was thus exerted selectively;
(ii) the biocidal activity of Pinosylvine was very markedly inferior to that of Triclosan on all the strains tested.

EXAMPLE 3

Deodorant Gel

| Sodium behenoyl lactylate | 10.00 g |
|---|---|
| Glycerol | 73.10 g |
| Pinosylvine | 0.75 g |
| Zinc ricinoleate | 1.00 g |
| Stearic acid | 8.40 g |
| Sodium hydroxide | 1.20 g |
| Fragrance, dyes | qs |
| Demineralized water qs | 100 g |

EXAMPLE 4

Water-in-Silicone Emulsion

| Silicone DC 245 Fluid (Dow Corning) | 6.60 g |
|---|---|
| Silicone DC 5225 C (Dow Corning) | 9.40 g |
| Ethyl alcohol | 11.00 g |
| Propylene glycol | 37.00 g |
| Pinosylvine | 0.50 g |
| Fragrance, preserving agents, dyes | qs |
| Demineralized water qs | 100 g |

EXAMPLE 5

Aqueous Stick

| Sodium stearate | 6.20 g |
|---|---|
| Pinosylvine | 1.00 g |
| Glycerol | 15.00 g |
| Propylene glycol | 20.00 g |
| Fragrance, preserving agents | qs |
| Demineralized water qs | 100 g |

EXAMPLE 6

Deodorant Cream

| Mixture of cetylstearyl alcohol and cetylstearyl alcohol oxyethylenated with 30 EO (Empiwax CL from the company Albright & Wilson) | 7.00 g |
|---|---|
| Mixture of glyceryl monostearate and glyceryl distearate (Cerasynt SD-V from the company ISP) | 2.00 g |
| Liquid petroleum jelly | 15.00 g |
| Glycerol | 20.00 g |
| Pinosylvine | 1.50 g |
| Fragrance, preserving agents | qs |
| Demineralized water qs | 100 g |

EXAMPLE 7

Deodorant Spray (Pump-Dispenser Bottle)

| Denatured 95 vol. % ethyl alcohol | 92.90 g |
|---|---|
| Zinc ricinoleate | 2.00 g |

-continued

| | |
|---|---|
| Pinosylvine | 1.00 g |
| Fragrance, dye | qs |

EXAMPLE 8

Anhydrous Antiperspirant Stick

| | |
|---|---|
| Stearyl alcohol | 22.00 g |
| Hydrogenated castor oil | 5.00 g |
| Isopropyl palmitate | 10.00 g |
| Aluminium chlorohydrate | 20.00 g |
| Pinosylvine | 3.00 g |
| Silicone D5 | 35.00 g |
| Talc | 5.00 g |

EXAMPLE 9

Deodorant Spray (Pressurized Flask)

| | |
|---|---|
| Denatured 95 vol % ethyl alcohol | 39.50 g |
| 3,5,3',4'-Tetrahydroxystilbene | 0.50 g |
| Isobutane | 60.00 g |

The foregoing written description relates to various embodiments of the present invention. Numerous changes and modifications may be therein without departing from the spirit and scope of the invention as defined in the following claims.

What is claimed is:

1. A method of inhibiting bacterial species chosen from *Corynebacterium xerosis* constituting the human skin flora comprising topically applying to the human skin 3,5-dihydroxystilbene in synthetic form or in the form of a plant extract containing it.

2. A method according to claim 1, wherein said plant extract is chosen from the genera Pinus; Alnus; Polygonum; Dalbergia; Scutellaria; and Lindera.

3. A method according to claim 2, wherein said plant extract is chosen from:

*Pinus montana mill., Pinus sylvestris L, Pinus contorta* var. *Latifolia S. Wats, Pinus ponderosa Dougl.,* and *Pinus Halpensis Mill.* from the Pinacea family;

*Alnus sieboldiana* from the Betulacea family;

*Polygonum nodosum* from the Polygonacea family;

*Dalbergia sissoo* from the Leguminosa family;

*Scutellaria scandens* from the Lamiacea family; and

*Lindera reflexa* from the Lauracea family.

4. A method according to claim 1, wherein said 3,5-dihydroxystilbene is a synthetic product.

5. A method according to claim 1, wherein said 3,5-dihydroxystilbene is derived from a plant extract containing it.

* * * * *

UNITED STATES PATENT AND TRADEMARK OFFICE
CERTIFICATE OF CORRECTION

PATENT NO. : 6,407,142 B1
DATED : June 18, 2002
INVENTOR(S) : Christophe Courbiere et al.

It is certified that error appears in the above-identified patent and that said Letters Patent is hereby corrected as shown below:

<u>Title page,</u>
Item [75], "Courbriere" should read -- Courbiere --.

Signed and Sealed this

Sixth Day of August, 2002

*Attest:*

JAMES E. ROGAN
*Attesting Officer*      *Director of the United States Patent and Trademark Office*